United States Patent
Katsoulis et al.

(10) Patent No.: US 8,865,850 B2
(45) Date of Patent: Oct. 21, 2014

(54) METHOD OF SELECTIVELY FORMING A REACTION PRODUCT IN THE PRESENCE OF A METAL SILICIDE

(71) Applicant: Dow Corning Corporation, Midland, MI (US)

(72) Inventors: Dimitris Katsoulis, Midland, MI (US); Robert Morgan, Midland, MI (US); Wendy Sparschu, Bay City, MI (US)

(73) Assignee: Dow Corning Corporation, Midland, MI (US)

( * ) Notice: Subject to any disclaimer, the term of this patent is extended or adjusted under 35 U.S.C. 154(b) by 17 days.

(21) Appl. No.: 13/688,813

(22) Filed: Nov. 29, 2012

(65) Prior Publication Data
US 2013/0334459 A1 Dec. 19, 2013

Related U.S. Application Data

(63) Continuation-in-part of application No. PCT/US2012/042475, filed on Jun. 14, 2012.

(51) Int. Cl.
C08G 77/60 (2006.01)
C07F 7/08 (2006.01)
C07F 7/21 (2006.01)
C07F 7/12 (2006.01)
C08L 83/16 (2006.01)

(52) U.S. Cl.
CPC ............ *C07F 7/0821* (2013.01); *C08G 77/60* (2013.01); *C07F 7/0805* (2013.01); *C07F 7/0896* (2013.01); *C07F 7/0827* (2013.01); *C07F 7/21* (2013.01); *C07F 7/125* (2013.01); *C08L 83/16* (2013.01)
USPC .............................................. 528/18; 528/14

(58) Field of Classification Search
CPC ........ C07F 7/0821; C07F 7/21; C07F 7/0896; C07F 7/125
USPC ...................................................... 528/14, 18
See application file for complete search history.

(56) References Cited

U.S. PATENT DOCUMENTS

| | | | |
|---|---|---|---|
| 2,865,939 A | 12/1958 | Little et. al. | |
| 2,888,476 A | 5/1959 | Little et. al. | |
| 4,698,218 A | 10/1987 | Belot et al. | |
| 4,824,918 A | 4/1989 | Bujalski et al. | |
| 4,973,725 A * | 11/1990 | Lewis et al. | ............... 556/472 |
| 5,120,406 A | 6/1992 | Shono et al. | |
| 5,357,019 A | 10/1994 | Weber et al. | |
| 6,174,982 B1 | 1/2001 | Nishida et al. | |
| 8,697,900 B2 | 4/2014 | Anderson et al. | |
| 8,772,525 B2 | 7/2014 | Katsoulis et al. | |
| 2003/0220514 A1 | 11/2003 | Lewis et al. | |
| 2008/0207430 A1 | 8/2008 | Clade et al. | |
| 2011/0132744 A1 | 6/2011 | Auner et al. | |

FOREIGN PATENT DOCUMENTS

| | | | |
|---|---|---|---|
| CN | 1880361 A | | 12/2006 |
| CN | 102502653 | | 6/2012 |
| GB | 629138 | | 6/1947 |
| WO | 2009067781 | * | 6/2009 |
| WO | 2011064174 A1 | | 6/2011 |
| WO | 2014028417 A2 | | 2/2014 |
| WO | 2014062255 A1 | | 4/2014 |

OTHER PUBLICATIONS

JP 2006-316197, Nov. 24, 2006, Nitto Kasei Co. Ltd., abstract only.
JP 2003-277507, Oct. 2, 2003, Osaka Gas Co. Ltd., abstract only.
JP 2006-188260, Jul. 20, 2006, Osaka Gas Co. Ltd., abstract only.
JP 2002-226586, Aug. 14, 2002, Osaka Gas Co. Ltd., abstract only.
JP 2001-122972, May 8, 2001, Osaka Gas Co. Ltd., abstract only.
JP 2001-048987, Feb. 20, 2001, Osaka Gas Co. Ltd., abstract only.
JP 11-349685, Dec. 21, 1999, Shin Etsu Chem. Co. Ltd., abstract only.
JP 10-182834, Jul. 7, 1998, Osaka Gas Co. Ltd., abstract only.
JP 09-255785, Sep. 30, 1997, Osaka Gas Co. Ltd., abstract only.
JP 06-256524, Sep. 13, 1994, Shono Tatsuya Osaka Gas Co. Ltd., abstract only.
JP 05-345825, Dec. 27, 1993 Mitsui Toatsu Chem. Inc., abstract only.
JP 04-178430, Jun. 25, 1992, Canon Inc., abstract only.
JP 03-104893, May 1, 1991, Nippon Carbon Co. Ltd., abstract only.
Moskovtsev, V.V., et. al. "Reactions for the Formation of Alkyl(Aryl)Chlorosilanes by Direct Systhesis", Izvestiya Akademil Nauk SSSR, Seriya Khimicheskaya, No. 3, pp. 609-614, Jul. 22, 1971.

(Continued)

*Primary Examiner* — Kuo-Liang Peng
(74) *Attorney, Agent, or Firm* — Catherine U. Brown

(57) ABSTRACT

A reaction product is formed utilizing a method that includes the step of combining a metal silicide and an aliphatic hydrocarbyl halide at a temperature of from 200° C. to 600° C. The aliphatic hydrocarbyl halide has the formula $H_aC_bX_c$, wherein a is 0 or more, b is 1 or more, c is one or more, and X is halo. The method allows the reaction product to be formed in a predictable and controlled manner. Moreover, the components used in this method can be easily recycled and/or re-used in other processes.

17 Claims, No Drawings

(56) References Cited

OTHER PUBLICATIONS

Sun, Wen, et. al. "Synthesis of carbosilane dendrimers with N,N-dimethylaniline as end groups", School of Chemistry and Chemical Engineering, Shandong University, Ji'nan, Peop. Rep. China. Chinese Chemical Letters (2009), 20 (3), 300-301. Publisher: Elsevier B.V. Abstract Only.

Lee, ChangYeob, et. al. "Synthesis of tris(silyl)methanes by modified direct process", Department of Chemistry, Mokpo National University, Chonnam, S. Korea. Bulletin of the Korean Chemical Society (2000), 21(10), 1020-1024. Publisher: Korean Chemical Society. Abstract Only.

Kashimura, Shigenori, et. al. "Practical method for the synthesis of polysilanes using Mg and Lewis acid system", Faculty of Science and Engineering, Kinki University, 3-4-1 Kowakae, Higashi-Osaka, Osaka, Japan. Tetrahedron Letters (2008), 49(2), 269-271. Publisher: Elsevier Ltd. Abstract Only.

Wang, Xinwei, et. al., "Electrosynthesis of Linear and Branched Methylene-Bridged Oligo- and Polycarbosilane", The Michael Szwarc Polymer Research Institute, Department of Chemistry, State University of New York-ESF, Syracuse, NY, USA. Macromolecules (Washington, DC, United States) (2007), 40(11), 3939-3950. Publisher: American Chemical Society. Abstract Only.

Ishifune, Manabu, " Electroreductive synthesis of oligosilanes and polysilanes with ordered sequences", Fac. Sci. Technol., Kinki Univ., 3-4-1 Kowakae, Higashi-osaka, Osaka, Japan. Yuki Gosei Kagaku Kyokaishi (2000), 58 (10), 966-974. Publisher: Yuki Gosei Kagaku Kyokai. Abstract Only.

Oshita, Joji, et. al., "Synthesis of Poly{[bis(ethynylphenyl)silylene]phenylene}s with Highly Heat-Resistant Properties", Department of Applied Chemistry Faculty of Engineering, Hiroshima University, Higashi-Hiroshima, Japan. Macromolecules (1999), 32(19), 5998-6002. Abstract Only.

Kashimura, Shigenori, et. al. "Electroreductive Synthesis of Polysilanes, Polygermanes, and Related Polymers with Magnesium Electrodes", Faculty of Science and Technology, Kinki University, Higashi-Osaka, Japan. Journal of Organic Chemistry (1999), 64(18), 6615-6621. Publisher: American Chemical Society. Abstract Only.

Comanita, Bogdan, et. al., "Synthesis of new carbosilane dendrimers with hydrophilic end-groups. Polyols", Institute for Chemical Process and Environmental Chemistry, National Research Council of Canada, Ottawa, ON, Can. Designed Monomers and Polymers (1999), 2(2), 111-124. Publisher: VSP BV. Abstract Only.

Ishifune, Manabu, et. al. "Electroreductive synthesis of sequence-ordered polysilanes using Mg electrodes", Department of Applied Chemistry, Faculty of Science and Technology, Kinki University, Higashi-Osaka, Japan. Editor(s): Torii, Sigeru. Novel Trends in Electroorganic Synthesis, [Papers presented at the International Symposium on Electroorganic Synthesis], 3rd, Kurashiki, Japan, Sep. 24-27, 1997 (1998), Meeting Date 1997, 371-372. Publisher: Springer, Tokyo, Japan. Abstract Only.

Yamanaka, Shoji, et. al. "New deintercalation reaction of calcium from calcium disilicide. Synthesis of layered polysilane", Dep. Appl. Chem., Hiroshima Univ., Hiroshima, Japan. Materials Research Bulletin (1996), 31(3), 307-16. Publisher: Elsevier. Abstract Only.

Ohshita, Joji, et. al. "Polymeric Organosilicon Systems. 22. Synthesis and Photochemical Properties of Poly[(disilanylene)oligophenylylenes] and Poly[(silylene)biphenylylenes]". Faculty of Engineering, Hiroshima University, Higashi-Hiroshima, Japan. Organometallics (1994), 13(12), 5002-12. Abstract Only.

Dahn, J.R., et. al. "Structure of siloxene and layered polysilane ($Si_6H_6$)", Dep. Phys., Simon Fraser Univ., Burnaby, BC, Can. Physical Review B: Condensed Matter and Materials Physics (1993), 48(24), 17872-7. Abstract Only.

Ohshita, Joji, et. al. "Polymeric organosilicon systems. 14. Synthesis and some properties of alternating polymers composed of a dithienylene group and a mono-, di- or trisilanylene unit", Fac. Eng., Hiroshima Univ., Higashi- Hiroshima, Japan. Applied Organometallic Chemistry (1993), 7(4), 269-77. Abstract Only.

Habel, Wolfgang, et. al., "Metalorganic synthesis of modified polycarbosilanes. I. Benzylidene-bridged polycarbosilanes", Fachbereich 6 (Chem), Univ.—GH Duisburg, Duisburg, Germany. Journal fuer Praktische Chemie/Chemiker-Zeitung (1993), 335(1), 61-8. Abstract Only.

Wang, Liming, et. al., "Synthesis and properties of novel comb polymers: unsaturated carbosilane polymers with pendent oligo(oxyethylene) groups", Hydrocarbon Res. Inst., Univ. South. California, Los Angeles, CA, USA. Macromolecules (1993), 26(5), 969-74. Abstract Only.

Shono, Tatsuya, et. al., "Electroreductive formation of polysilanes", Fac. Eng., Kyoto Univ., Kyoto, Japan. Journal of the Chemical Society, Chemical Communications (1990), (17), 1160-1. Abstract Only.

Ouyang, Gan, "Polysilanes and polycarbosilanes: synthesis by wurtz coupling and attempted synthesis from metal silicides", Univ. of Akron, Akron, OH, USA. Avail. UMI, Order No. DA9802149. (1996), 130 pp. From: Diss.Abstr. Int., B 1998, 58(7), 3628. Abstract Only.

Walter, et. al., "Mechanism of the silicide-catalysed hydrodehalogenation of silicon tetrachloride to trichlorosilane", J. Chem. Soc., Faraday Trans., 1996, pp. 4605-4608, 92(22), Freiberg, Germany.

* cited by examiner

METHOD OF SELECTIVELY FORMING A REACTION PRODUCT IN THE PRESENCE OF A METAL SILICIDE

CROSS REFERENCE TO RELATED APPLICATION

This application is a continuation in part of U.S. patent application Ser. No. PCT/US12/042475, filed on 14 Jun. 2012 and claims priority thereto under 35 U.S.C. §120 and 35 U.S.C. §365(c). U.S. Patent Application Ser. No. PCT/US12/042475 is hereby incorporated by reference.

BACKGROUND

Polysilanes and polycarbosilanes are well known in the art and tend to have either an all silicon backbone —(Si—Si)— or a silicon-carbon backbone —(Si—C)—, respectively. Polysilanes are typically formed in a Wurtz coupling process using, as one example, $Me_2SiCl_2$, sodium or potassium metal, toluene, and heat. This process is time consuming, expensive, and difficult to implement on a production scale because metals such as sodium and potassium are pyrophoric, difficult to handle, and costly. In addition, this process generates inorganic salts as by-products which need to be disposed of and/or recycled, thereby further increasing production complexities and costs. Since scaling up this process to commercial production scale is not practical, the large scale production of polysilanes tends to be difficult and expensive.

Polycarbosilanes are typically formed using Grignard reactions of chloromethyltrichlorosilanes, ring-opening polymerization reactions of 1,3-disilacyclobutane derivatives, and/or hydrosilylation reactions of vinyl silanes. These reactions tend to be inefficient and expensive and tend to generate unwanted by-products that lower the yield of the polycarbosilanes. In addition, it is both costly and difficult to recycle the by-products and other remnants of these reactions. Accordingly, scaling up these reactions to commercial production scale is also not practical. Just as above, this difficulty in scaling makes the large scale production of polycarbosilanes difficult and expensive. As a result of the aforementioned production difficulties, there remains an opportunity to develop an improved process for forming both polysilanes and polycarbosilanes.

SUMMARY OF THE DISCLOSURE

The instant disclosure provides a method of forming a reaction product in the presence of a metal silicide. The method includes the step of combining the metal silicide and an aliphatic hydrocarbyl halide in a reactor at a temperature of from 200° C. to 600° C. to form the reaction product.

DETAILED DESCRIPTION OF THE DISCLOSURE

The present disclosure provides a method of forming a reaction product. The reaction product is typically a mixture. The mixture may include at least one polysilane and/or at least one polycarbosilane. As is well known in the art, polysilanes typically have a backbone of silicon atoms bonded to each other (Si—Si bonds) while polycarbosilanes typically have a backbone of silicon atoms bonded to carbon atoms (Si—C—Si bonds). Illustrative, but non-limiting, examples of typical polysilanes and polycarbosilanes are set forth immediately below:

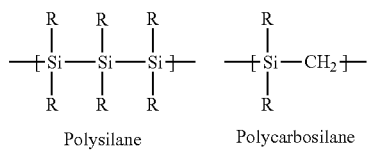

Polysilane    Polycarbosilane

In the aforementioned structures, "R" is merely shown as a placeholder, is non-limiting, and does not represent any particular atom or compound. Other non-limiting examples are similar to those above and include pendant silicon atoms bonded to backbone carbon atoms, pendant carbon atoms bonded to backbone silicon atoms, and/or pendant silicon atoms bonded to backbone silicon atoms. Each of the at least one polysilane and the at least one polycarbosilane may be linear, branched, or cyclic. In other words, the mixture of the at least one polysilane and the at least one polycarbosilane may include one or more linear, branched, or cyclic polysilanes and one or more linear, branched, or cyclic polycarbosilanes. In addition, there can be both Si—C—Si and Si—Si bonds in the same molecular, e.g., a mixed polysilane/polycarbosilane molecule.

Polysilanes:

In one embodiment, the mixture includes at least one polysilane that has the formula $R_3Si—(R_2Si)_m—SiR_3$ wherein each R may be the same or different from one another and each R is independently a $C_1$-$C_{20}$, $C_1$-$C_{10}$, and/or a $C_1$-$C_4$ alkyl, aryl, alkaryl or aralkyl (group) and where m has a value of from 1 to 100. Alternatively, it is contemplated that one or more R groups may be —H, i.e., a hydrogen atom. In addition, it is contemplated that R can be a halogen atom, such as Cl. In alternative embodiments, m has an average value of from 1 to 15, from 2 to 14, from 3 to 13, from 4 to 14, from 5 to 13, from 6 to 12, from 7 to 11, from 8 to 10, from 9 to 10, from 1 to 5, from 1 to 4, from 1 to 3, from 1 to 2, from 2 to 5, from 2 to 3, from 2 to 4, from 3 to 5, or from 3 to 4. The mixture may also include a disilane where m=0. Of course, the disclosure is not limited to these particular values of m and the value of m may be any value or range of values, both whole and fractional, within those ranges and values described above.

At least one polysilane may be branched. Although not particularly limited, the branched polysilane typically has only one silicon side chain per molecule but may have two or more. In still another embodiment, at least one polysilane is cyclic. Typically, the cyclic polysilane has from 4 to 12, from 4 to 10, or from 4 to 8, silicon atoms. It is also contemplated that the mixture may include at least two polysilanes and at least one of the polysilanes may be branched and/or at least one of the polysilanes may be cyclic.

Polycarbosilanes:

At least one polycarbosilane may have the formula $R^2_3Si—CH_2(R^2_2Si—CH_2)_nSiR^2_3$ wherein each $R^2$ may independently be the same or different than R above and n may be the same or different from m above. It is to be understood that, in the same mixture, each of R and $R^2$ and m and n can differ from each other in each polysilane and polycarbosilane. In one embodiment, the mixture includes a carbodisilane wherein n=0. In another embodiment, at least one polycarbosilane is branched. Although not particularly limited, the branched polycarbosilane typically has only one side chain per molecule but may have two or more. In still another embodiment, at least one polycarbosilane is cyclic. Typically, the cyclic polycarbosilane has from 2 to 4 or 2 to 3 silicon atoms. These cyclic polycarbosilanes are not particularly limited and one or more may be selected from the group of 1,1,3,3-tetramethyl-1,3disilacyclobutane, 1,1,3,3,-tetraethyl-1,3-disilacyclopentane, 1,1,3,3,5-pentamethyl-1,3,5-trisilacylohexane, 1,1,3,3,5,5-hexamethyl-1,3,5-trisilacylohexane, and combinations thereof. Alternatively, the mixture may include at least two polycarbosilanes and at least one of the polycarbosilanes may be branched and/or at least one of the polycarbosilanes may be cyclic.

The mixture may alternatively include at least two polysilanes and at least two polycarbosilanes wherein at least one of the polysilanes and/or at least one of the polycarbosilanes is cyclic. In another embodiment, the mixture includes at least two polysilanes and at least two polycarbosilanes wherein at least one of the polysilanes and/or at least one of the polycarbosilanes is branched.

Additional Polysilanes/Polycarbosilanes:

It is also contemplated that the mixture may include one or more mixed or hybrid polysilane-polycarbosilanes. Mixed or hybrid polysilane-polycarbosilanes include both Si—Si bonds and Si—C bonds in the backbone. Typically, mixed or hybrid polysilane-polycarbosilanes include polysilane portions or blocks and polycarbosilane portions or blocks, as shown strictly for illustrative purposes below wherein m and/or n may independently be the same or different from m and/or n described above and each $R^3$ is independently chosen and may be the same or different from R and $R^2$ described above:

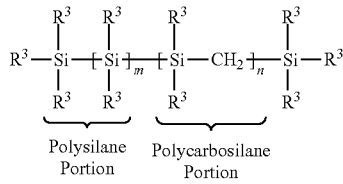

Polysilane Portion    Polycarbosilane Portion

It is also contemplated that the mixture may include one or more compounds of the following formulas: $X_3Si—(X_2Si—SiX_2)_a—SiX_3$ and $X'_3Si—CH_2—(X'_2Si—CH_2)_b—SiX'_3$, wherein $0 \leq a, b < 20$, and each of X and X' is independently Cl, H or Me. It is also contemplated that each of X and X' may independently be $C_1$-$C_{10}$ or $C_1$-$C_4$ or halo. In various embodiments, at the beginning of the reaction to form the mixture, X has a tendency to be Me or H. Then, at the end of the reaction, X has a tendency to be Cl more often. In other embodiments, branched analogues of the aforementioned compounds and/or compounds of the following formula: $Me_3Si—Me_2Si—CH_2—SiMe_3$, are included in the mixture.

In still other embodiments, the mixture includes one or more halopolysilanes and/or one or more halopolycarbosilanes. The halo atoms of these compounds are not particularly limited and may include fluoro, chloro, bromo, and/or iodo atoms. In various other embodiments, the mixture also includes one or more silicon monomer(s) selected from the group of $SiH_4$, $Me_4Si$, $Me_3SiH$, $Me_3SiCl$, $Me_2SiCl_2$, $Me_2HSiCl$, $MeSiCl_3$, $MeHSiCl_2$, $SiCl_4$, $EtSiCl_3$, n-$PrSiCl_3$, Allyl-$SiCl_3$, silacyclobutane, $Me_2EtSiCl$, $MeEtSiCl_2$, t-$BuMe_2SiCl$, $Me_3SiCH_2C \equiv CCH_3$, and combinations thereof.

In still other embodiments, one or more cyclic or branched species such as those described immediately below may be present in the mixture:

$(CH_2SiR_2)_f$ wherein each R is independently Cl, Me, Et, H; f>3;

$(CH_2SiR_2)_f(OSiR_2)_e$ wherein each R is independently chosen from Cl, Me, Et, H; (f+e)>3;

$(SiR_2)_f$ wherein each R is independently Cl, Me, Et, H; f>3

$(SiR_2)_f(CH_2SiR_2)_e$ wherein each R is independently Cl, Me, Et, H; (f+e)>3;

$R_2Si(CR_2)_3$ wherein each R is independently Cl, Me, Et, H;

$R_3Si(SiR_2)_f[SiR(SiR_3)](SiR_2)_eSiR_3$ wherein each R is independently chosen from Cl, Me, Et, H; f>0, e>0;

$R_3Si(SiR_2)_f[SiR(CH_2SiR_3)](SiR_2)_eSiR_3$ wherein each R is independently chosen from Cl, Me, Et, H; f>0, e>0;

$R_3Si(CH_2SiR_2)_f[CH_2SiR(SiR_3)](CH_2SiR_2)_eCH_2SiR_3$ wherein each R is independently chosen from Cl, Me, Et, H; f>0, e>0;

$R_3Si(CH_2SiR_2)_f[CH(SiR_3)SiR_2](CH_2SiR_2)_eCH_2SiR_3$ wherein each R is independently chosen from Cl, Me, Et, H; f>0, e>0;

$R_3Si(CH_2SiR_2)_f[CH(R)SiR_2](CH_2SiR_2)_eCH_2SiR_3$ wherein each R is independently chosen from Cl, Me, Et, H; f>0, e>0;

$R_3Si(CH_2SiR_2)_f[CH_2SiR(CH_2SiR_3)](CH_2SiR_2)_eCH_2SiR_3$ wherein each R is independently chosen from Cl, Me, Et, H; f>0, e>0;

$(R_3Si)_3CH$ wherein each R is independently chosen from Cl, Me, Et, H;

$(R_3Si)_3C—CH_3$ wherein each R is independently chosen from Cl, Me, Et, H;

$(R_3Si)_2C=CH_2$ wherein each R is independently chosen from Cl, Me, Et, H;

$R_3Si(CH_2SiR_2)_g(SiR_2)_h[SiR(SiR_3)](SiR_2)_e(CH_2SiR_2)_f SiR_3$ wherein each R is independently chosen from Cl, Me, Et, H; g>0, h>0, f>0, e>0;

$R_3Si(CH_2SiR_2)_g(SiR_2)_h[SiR(CH_2SiR_3)](SiR_2)_e(CH_2SiR_2)_f SiR_3$ wherein each R is independently chosen from Cl, Me, Et, H; g>0, h>0, f>0, e>0;

$R_3Si(SiR_2)_g(CH_2SiR_2)_h[CH_2SiR(SiR_3)](CH_2SiR_2)_e(SiR_2)_f CH_2SiR_3$ wherein each R is independently chosen from Cl, Me, Et, H; g>0, h>0, f>0, e>0;

$R_3Si(SiR_2)_g(CH_2SiR_2)_h[CH(SiR_3)SiR_2](CH_2SiR_2)_e(SiR_2)_f CH_2SiR_3$ wherein each R is independently chosen from Cl, Me, Et, H; g>0, h>0, f>0, e>0;

$R_3Si(SiR_2)_g(CH_2SiR_2)_h[CH(R)SiR_2](CH_2SiR_2)_e(SiR_2)_f CH_2SiR_3$ wherein each R is independently chosen from Cl, Me, Et, H; g>0, h>0, f>0, e>0; and $R_3Si(CH_2SiR_2)_f[CH_2SiR(CH_2SiR_3)](CH_2SiR_2)_e(SiR_2)_f CH_2SiR_3$ wherein each R is independently chosen from Cl, Me, Et, H; f>0, e>0.

Additional multiple branched, longer chain branched, and/or more complex mixed carbosilane/polysilane compounds may also be included in the mixture.

Additional compounds may also be formed by the method of this disclosure. These compounds include, but are not limited to, straight chain polysilanes, straight chain carbosilanes, and mixed carbo/polysilanes. Suitable but non-limiting examples of straight chain polysilanes have the formula $R_3Si(SiR_2)_f SiR_3$ wherein $f \geq 0$ and each R is independently H, Methyl (or other hydrocarbon), or Cl (or other halogen). Suitable but non-limiting examples of straight chain carbosilanes have the formula $R_3SiCH_2(SiR_2CH_2)_f SiR_3$ wherein $f \geq 0$ and each R is independently from H, Methyl (or other hydrocarbon), or Cl (or other halogen). Suitable but non-limiting examples of mixed carbo/polysilanes have one or more of the following formulae: $R_3SiCH_2(SiR_2CH_2)_e(SiR_2)_f SiR_3$ ($e \geq 0$, f>0); $R_3Si(SiR_2CH_2)_e(SiR_2)_f SiR_3$ (e>0, $f \geq 0$); $R_3SiCH_2(SiR_2)_m(SiR_2CH_2)_n SiR_3$ (e>0, f>0); $R_3SiCH_2(SiR_2)_g(SiR_2CH_2)_e(SiR_2)_f SiR_3$ (g, e, f>0); $R_3SiCH_2(SiR_2CH_2)_g(SiR_2)_e(SiR_2CH_2)_b SiR_3$ (g, e, f>0); $R_3Si(SiR_2)_g(SiR_2CH_2)_e(SiR_2)_b SiR_3$ (g, e, f>0); and $R_3Si(SiR_2CH_2)_g(SiR_2)_e(SiR_2CH_2)_f SiR_3$ (g, e, f>0), wherein for each of the aforementioned formulae, each R is independently H, Methyl (or other hydrocarbon), or Cl (or other halogen). Additional more complex mixed carbo/polysilanes including groups similar to g, e and f are also contemplated herein.

The mixture is not particularly limited relative to amount of the at least one polycarbosilane, and when present, the amount of the at least one polysilane. It is contemplated that the at least one polysilane may be present in the mixture in amounts of from 0 to 99, alternatively 1 to 99, alternatively 5 to 95, alternatively 10 to 90, alternatively 15 to 85, alternatively 20 to 80, alternatively 25 to 75, alternatively 30 to 70, alternatively 35 to 65, alternatively 40 to 60, alternatively 45 to 55, or alternatively 45 to 50, weight percent based on a total weight of the mixture. The at least one polycarbosilane may be present in the same or similar amounts. In one embodiment, the at least one polysilane and the at least one polycarbosilane are each present in amounts of 50 weight percent based on a total weight of the mixture. Additionally, the one or more mixed or hybrid polysilane-polycarbosilanes may be present in the mixture in amounts of from 0.1 to 20, of from 0.1 to 10, or of from 0.1 to 5, weight percent based on a total weight of the mixture. The one or more halopolysilanes and/or one or more halopolycarbosilanes may be present in the mixture in amounts of from 0.1 to 20, of from 0.1 to 10, or of from 0.1 to 5, weight percent based on a total weight of the mixture. The one or more silicon monomer(s) may be present in the mixture in amount of from 0.1 to 99, from 0.5 to 50, from 1 to 50, from 5 to 50, or from 5 to 25, weight percent based on a total weight of the mixture. The disclosure is not limited to any of the aforementioned values and any one or more of those values may be further defined as a particular value or range of particular values, both whole and fractional, within those ranges described above.

Alternatively, the mixture may consist of, or consist essentially of, the at least one polysilane and the at least one polycarbosilane. It is also contemplated that the mixture may consist of or consist essentially of the at least one polysilane and the at least one polycarbosilane in addition to one or more of the mixed or hybrid polysilane-polycarbosilanes, silicon monomer(s), halopolysilanes and/or halopolycarbosilanes. In various embodiments wherein the mixture consists essentially of the at least one polysilane and the at least one polycarbosilane, the mixture is free of, or includes less than 10, 5, or 1, weight percent of other chlorinated (or halogenated) species such as $CCl_4$, $SiH_4$, other silanes, monomethyltrichlorosilane, and/or any of the silicon monomers described above, and/or combinations thereof, based on a total weight of the mixture. It is also contemplated that the mixture consisting essentially of the polysilane and the polycarbosilane may include the silicon monomer(s) or may be free of the silicon monomer(s). It is further contemplated that the aforementioned description of weight percents may apply to embodiments wherein the mixture consists essentially of the at least one polysilane and the at least one polycarbosilane in addition to one or more of the mixed or hybrid polysilane-polycarbosilanes, silicon monomer(s), halopolysilanes and/or halopolycarbosilanes. In other embodiments, the terminology "consisting essentially of" describes the mixture being free of compounds, known to those of skill in the art, that materially affect the overall composition of the mixture.

Alternatively, it is contemplated that the mixture may comprise one or more silicon monomers, as described above. The silicon monomers include $SiH_4$, $Me_4Si$, $Me_3SiH$, $Me_3SiCl$, $Me_2SiCl_2$, $Me_2HSiCl$, $MeSiCl_3$, $MeHSiCl_2$, $SiCl_4$, $EtSiCl_3$, n-$PrSiCl_3$, Allyl-$SiCl_3$, silacyclobutane, $Me_2EtSiCl$, MeEtSi$Cl_2$, t-$BuMe_2SiCl$, $Me_3SiCH_2C\equiv CCH_3$, and combinations thereof. Alternatively, the method described herein may be used to form a mixture comprising $SiCl_4$ and $HSiCl_3$, and combinations thereof. Alternatively, the mixture may consist of, or consist essentially of, one or more of the silicon monomers.

Method of Forming the Mixture:

Referring back to the method itself, the method includes the step of combining ingredients comprising a metal silicide and an aliphatic hydrocarbyl halide in a reactor at a temperature of from 200° C. to 600° C. to form the mixture. The metal silicide is typically further defined as $Mg_2Si$ but is not limited to this compound. It is contemplated that the metal silicide may be further defined as a Group I or Group II metal silicide, i.e., a silicide including a metal from Group I or Group II of the periodic table of the elements. Alternatively, the metal may be a Group metal, such as Li, Na, K, Rb, or Cs. Alternatively, the metal may be a Group II metal, such as Mg, Ca, Sr, or Ba. Alternatively, more than one silicide and/or mixed silicides can be utilized. The metal silicide is typically a solid and may have a particle size of 1 in, ⅞ in., ¾ in., ⅝ in., 0.530 in., ½ in., 7⁄16 in., ⅜ in., 5⁄16 in., 0.265 in., or ¼ in., or a mesh size of Nos. 3.5, 4-8, 10, 12, 14, 16, 18, 20, 25, 30, 35, 40, 45, 50, 60, 70, 80, 100, 120, 140, 170, 200, 230, 270, 325, 400, etc., mesh. The disclosure is not limited to any of the aforementioned particular values or ranges of values and the particle size may be any value or range of values, both whole and fractional, within those ranges and values described above.

The method may further comprise an activation step performed before combining the aliphatic hydrocarbyl halide and the metal silicide. Without wishing to be bound by theory, it is thought that temperature and time for activation are selected to be sufficient to remove oxide layers from the surface of the metal silicide, if present. As used herein, "activation" and its derivatives such as "activate" and "activating" means to contact the metal silicide with hydrogen at elevated temperature. The temperature may be, for example, 400° C. to 600° C., alternatively 500° C. The time for activation may be 1 hour or more, alternatively 1 hour to 2 hours.

The aliphatic hydrocarbyl halide is a compound of formula $H_aC_bX_c$, where subscript a represents average number of hydrogen atoms present, subscript b represents average number of carbon atoms present, and subscript c represents average number of halogen atoms present. Subscript a is an integer of 0 or more, subscript b is an integer of 1 or more, and subscript c is an integer of 1 or more. When the organohalide is a noncyclic aliphatic hydrocarbyl halide, then a quantity (a+c)=a quantity (2b+2). When the organohalide is a monocyclic aliphatic hydrocarbyl halide, then the quantity (a+c)=2b. Each X is independently halo, i.e., a halogen atom. Alternatively, subscript c may have a value of at least 2, alternatively 2 to 4. Examples of suitable organohalides include, but are not limited to, methyl chloride ($H_3CCl$), methylene chloride ($H_2CCl_2$), chloroform ($HCCl_3$), and carbon tetrachloride ($CCl_4$).

Alternatively, the aliphatic hydrocarbyl halide may be an alkyl halide of formula RX, e.g., when subscript c is 1; wherein R is $C_1$-$C_{10}$ alkyl and X is halo, as described above. It is also contemplated that R may be $C_1$-$C_4$ alkyl. The $C_1$-$C_{10}$ (or $C_1$-$C_4$) alkyl is not particularly limited and any alkyl group having 1, 2, 3, 4, 5, 6, 7, 8, 9, or 10 carbon atoms may be utilized including isomers thereof. Similarly, any halo atom, i.e., Br, Cl, F, or I, can be used. Typically, the alkyl halide is further defined as MeCl and/or propyl chloride.

It is also contemplated that mixtures of aliphatic hydrocarbyl halides can be used so long as at least one aliphatic hydrocarbyl halide of the mixture is of the aforementioned formula. In other words, the mixture of aliphatic hydrocarbyl halides can include one or more aliphatic hydrocarbyl halides that differ from the aforementioned formula so long as at least one aliphatic hydrocarbyl halide of the aforementioned formula is utilized.

In one embodiment, the method includes the step of combining $Mg_2Si$ (i.e., the metal silicide) and the aliphatic hydrocarbyl halide in a reactor at a temperature of from 200° C. to 600° C. to form the mixture. Typically, the formation of stable salts drive the formation of the mixture including the at least one polysilane and the at least one polycarbosilane. The step of combining may be further defined as reacting the $Mg_2Si$ and the aliphatic hydrocarbyl halide. The $Mg_2Si$ and the aliphatic hydrocarbyl halide are typically reacted in approximately equal molar ratios but the amounts of each are not particularly limited. In one embodiment, the aliphatic hydrocarbyl halide is passed over the $Mg_2Si$ in a flow reactor until no additional reaction occurs or until undesired selectively of products begins. Typically, once all of the silicon is reacted and/or all of the Mg is reacted (to form, for example, $MgCl_2$ by taking up chlorine) then the reaction will cease.

In one embodiment, e.g., when the aliphatic hydrocarbyl halide is a liquid at ambient conditions, a carrier may be used to facilitate combining the metal silicide and the aliphatic hydrocarbyl halide. For example, the aliphatic hydrocarbyl halide may be combined with a carrier gas before contacting the resulting gaseous combination with the metal silicide. The carrier gas may be an inert gas, such as nitrogen, helium, or argon; or the carrier gas may be $H_2$; or a combination thereof. Alternatively, when the aliphatic hydrocarbyl halide is a liquid or solid, the method may further comprise pre-heating and gasifying the aliphatic hydrocarbyl halide before it is introduced into the reactor.

The metal silicide (e.g., the $Mg_2Si$) and the aliphatic hydrocarbyl halide react in a reactor in a continuous, semi-continuous, or batch mode. Most typically, the reactor is a continuous reactor. The particular type of reactor is not limited and may be further defined as a fluidized bed reactor, a gas phase heterogeneous reactor, a fixed bed reactor, etc. The length and size of the reactor are also not particularly limited. Typically, the length and volume of the reactor is sufficient to achieve adequate residence time of contact of the aliphatic hydrocarbyl halide with the silicide. Typical, but non-limiting, residence times are from 0.1 to 100, from 0.1 to 30, from 0.5 to 20, or from 1 to 10, seconds. As appreciated by those of skill in the art, the terminology "residence time" describes an average amount of time the aliphatic hydrocarbyl halide spends in the reactor before exiting such that it contacts the silicide.

In one embodiment, the metal silicide (e.g., the $Mg_2Si$) is stationary and the aliphatic hydrocarbyl halide is passed through and/or over the $Mg_2Si$. In this embodiment, the aliphatic hydrocarbyl halide has a residence time in or over the metal silicide of from 0.1 to 10, from 0.5 to 10, from 0.5 to 9.5, from 1 to 8.5, from 1.5 to 8, from 2 to 7.5, from 3 to 7, from 3.5 to 6.5, from 4 to 6, from 4.5 to 5.5, or of 5, seconds. It is contemplated that these residence times may be increased or decreased appropriately depending on the size of the reactor, the conditions of reaction, and the desired products. It is to be understood that an increase in reactor size does not necessarily increase residence time. In fact, an increase in reactor size may decrease residence time. The aliphatic hydrocarbyl halide and the metal silicide typically react for a total time of from minutes to hours. In other words, the entire reaction (and not any one particular residence time) typically occurs for a time of from minutes to hours. In various embodiments, the metal silicide and the aliphatic hydrocarbyl halide react for a time of from 1 to 60 minutes, from 1 to 40 minutes, from 1 to 20 minutes, from 1 to 24 hours, from 1 to 15 hours, from 1 to 10 hours, from 1 to 5 hours, etc.

In addition, the reactor temperature is not particularly limited within the aforementioned range and may be further defined as from 210 to 590, from 220 to 580, from 230 to 570, from 240 to 560, from 250 to 550, from 260 to 540, from 270 to 530, from 280 to 520, from 290 to 510, from 300 to 500, from 310 to 490, from 320 to 480, from 330 to 470, from 340 to 460, from 350 to 450, from 360 to 440, from 370 to 430, from 380 to 420, from 390 to 410, of from 325 to 500, or of 400, ° C. Temperatures above 600° C. tend to cause decomposition of aliphatic hydrocarbyl halides. Temperatures less than 200° C. tend to be ineffective in promoting reaction.

The selectivity of the reaction of the aliphatic hydrocarbyl halide can be controlled by selection of the silicide, selection of the aliphatic hydrocarbyl halide, and by the temperature used in the method, as shown below in the examples. For example, when using $Mg_2Si$ as the metal silicide and $CCl_4$ as the aliphatic hydrocarbyl halide, the products of reaction above 450° C. included 3 types of silicon compounds, i.e., monomers, siloxanes, and silmethylenes. Under these conditions, the $Mg_2Si$ participated in the reaction as a reactant. However, when lower reaction temperature was used, the reaction produced primarily chlorinated hydrocarbon products when temperature was started at 200° C. and increased to 400° C. However, when $Mg_2Si$ was used as the metal silicide and $CCl_4$ was used as the aliphatic hydrocarbyl halide, the products of the reaction were primarily silicon monomers, e.g., $SiCl_4$ when temperature was above 400° C. Without wishing to be bound by theory, it is thought that the $Mg_2Si$ participated in the reaction as a catalyst at lower temperatures, e.g., 200° C. to 400° C., until temperature reached 400° C., when the $Mg_2Si$ became susceptible to reaction itself. Without wishing to be bound by theory, it is thought that this phenomenon may be due to the mobility of the silicon within the metal silicide, which below certain temperatures is thought to be less mobile than at higher temperatures. The polarizability of the reactant gas may also have an effect. For example, $CCl_4$ has no dipole moment, so $CCl_4$ is non-polarizable on the surface, and it is thought this may tailor some of the reaction products at lower temperatures (e.g., less than 400° C. for $Mg_2Si$). As the temperature increases, the bonds become more labile, so it is thought that higher temperatures make it possible to break some of the C—Cl bonds to form chlorinated products and $MgCl_2$ and to permit the $Mg_2Si$ to act as a reactant and not just as a catalyst.

The metal silicide and the aliphatic hydrocarbyl halide also typically react at atmospheric pressure or higher but this disclosure is not limited to any particular pressure. In various embodiments, the pressure is further defined as 0.5, 1, 1.5, 2, 2.5, 3, 3.5, 4, 4.5, 5, or 5+, atmospheres. The metal silicide and the aliphatic hydrocarbyl halide react to form the mixture having yields of the at least one polysilane and/or the at least one polysilane of at least 30, 35, 40, 45, 50, 55, 60, 65, 70, 75, 80, 85, 90, 95, or 95+, percent yield. The disclosure is not limited to any of the aforementioned values and any one or more of those values may be further defined as a particular value or range of particular values, both whole and fractional, within those ranges described above.

In additional embodiments, the method is further defined as a method of forming the mixture includes at least one linear polysilane, at least one linear polycarbosilane, and at least one cyclic polycarbosilane in the presence of $Mg_2Si$ wherein the method includes the step of combining the $Mg_2Si$ and methyl chloride in a continuous fluidized bed reactor at a temperature of from 200° C. to 600° C. to form the mixture. In this embodiment, at least one polysilane has the formula $X_3Si$—$(X_2Si$—$SiX_2)_a$—$SiX_3$ and at least one polycarbosilane has the formula $X'_3Si$—$CH_2$—$(X'_2Si$—$CH_2)_b$—$SiX'_3$, wherein 0≤a, b<20, and each of X and X' is independently Cl, H or Me. In another embodiment, X of the at least one polysilane is further defined as methyl. In still another embodiment, the mixture includes at least one additional polycarbosilane that is selected from the group of 1,1,3,3-tetramethyl-1,3 disilacyclobutane, 1,1,3,3,-tetramethyl-1,3-disilacyclopentane, 1,1,3,3,5-pentamethyl-1,3,5-trisilacylohexane, 1,1,3,3,5,5-hexamethyl-1,3,5-trisilacylohexane, and combinations thereof. In a further embodiment, the mixture further includes at least one silicon monomer selected from the group of $Me_4Si$, $Me_3SiH$, $Me_3SiCl$, $Me_2SiCl_2$, $Me_2HSiCl$, $MeSiCl_3$, $MeHSiCl_2$, $SiCl_4$, $EtSiCl_3$, $n\text{-}PrSiCl_3$, $Allyl\text{-}SiCl_3$, silacyclobutane, $Me_2EtSiCl$, $MeEtSiCl_2$, $t\text{-}BuMe_2SiCl$, $Me_3SiCH_2C\equiv CCH_3$, and combinations thereof.

The method of this disclosure tends to form high yield mixtures of the at least one polysilane and the at least one polycarbosilane. Additionally, the method of preparing the mixture is time and cost effective and allows the mixture to be formed in a predictable and controlled manner. Moreover, the components used in this method can be easily recycled and/or re-used in other processes. Furthermore, this method tends to increase industrial safety, tends to minimize production complexities (e.g., can utilize fluid or vibrating beds), and allows for customization/tuning of selectivity of which products are formed in the mixture, e.g., monosilanes, halogenated hydrocarbons, polysilanes, and/or polycarbosilanes are formed by manipulating silicide content, temperature, residence time, and halogen content.

The method may further comprise recovering one or more of the products from the mixture produced. The polycarbosilane may be recovered by, for example, removing gaseous mixture from the reactor followed by condensation. The mixture may be separated by distillation.

EXAMPLES

A mixture of the instant disclosure was formed along with comparative mixtures that are not representative of this disclosure. These mixtures were then analyzed to determine their contents.

Example 1

Formation of One Embodiment of the Instant Disclosure

To form the mixture, $Mg_2Si$ (Sigma Aldrich, 99+%) in an amount 0.32 g (i.e., a Group II metal silicide) was loaded into a quartz glass tube inside of an inert glove box. The quartz tube was then inserted into a flow reactor, and during the insertion, the $Mg_2Si$ was briefly exposed to atmospheric (i.e., non-dry) air (10-20 seconds maximum). The reactor was then quickly purged with $H_2$ to remove any remaining atmospheric air. Activation of the $Mg_2Si$ was then performed with 100 sccm $H_2$ (controlled via Omega FMA 5500 mass flow controller) at 500° C. (heated in a Lindberg/Blue Minimite 1" tube furnace). Afterwards, the temperature of the reactor was reduced to 400° C., the $H_2$ flow was shut off and a flow of 50 sccm of Ar was utilized for 30 minutes to purge the reactor of all $H_2$.

After purging with Ar, the reaction was started by shutting off the Ar and flowing MeCl (i.e., a Cl alkyl halide) through the reactor at a rate of 5 sccm. The reaction was then periodically sampled over 60 min by GC/GC-MS to monitor the amounts of various reaction products that were formed. The effluent of the reactor passed through an actuated 6-way valve (Vici) with constant 100 μL injection loop before being discarded. Samples were taken from the reaction stream by actuating an injection valve and a 100 μL sample was passed directly into the injection port of a 7890A Agilent GC-MS for analysis with a split ratio at the injection port of 100:1. The GC included two 30 m SPB-Octyl columns (Supelco, 250 μm inner diameter, 0.25 um thick film) which were placed in parallel such that the sample was split evenly between the two columns. One column was connected to a TCD detector for quantification of the reaction products and the other column was connected to a mass spectrometer (Agilent 7895C MSD) for sensitive detection of trace products and positive identification of any products that formed. Rather than being heated in a GC oven, the columns were heated by an Agilent LTM module, i.e., the columns were wrapped with heating elements and thermocouples such that they were precisely and rapidly ramped to the desired temperature. This low thermal mass system allowed rapid analysis (as little as 7 minutes between sample injections). All steps were performed at atmospheric pressure.

The mixture formed using the aforementioned procedure included numerous linear oligomeric polysilanes and polycarbosilanes of the formulas $X_3Si\text{—}(X_2Si\text{—}SiX_2)_a\text{—}SiX_3$ and $X'_3Si\text{—}CH_2\text{—}(X'_2Si\text{—}CH_2)_b\text{—}SiX'_3$, where 0≤a, b<20, and each of X and X' are independently Cl, H or Me. At the beginning of the reaction, X had a tendency to be Me or H. Then, at the end of the reaction, X had a tendency of be Cl more often. In this mixture, mixed polysilane/carbosilanes including some of the formula $Me_3Si\text{—}Me_2Si\text{—}CH_2\text{—}SiMe_3$ were also included. The mixture also included cyclic carbosilanes including 1,1,3,3-tetramethyl-1,3 disilacyclobutane; 1,1,3,3,-tetramethyl-1,3-disilacyclopentane; 1,1,3,3,5-pentamethyl-1,3,5-trisilacylohexane; and 1,1,3,3,5,5-hexamethyl-1,3,5-trisilacylohexane. In addition, the mixture included various Si monomers including $Me_4Si$, $Me_3SiH$, $Me_3SiCl$, $Me_2SiCl_2$, $Me_2HSiCl$, $MeSiCl_3$, $MeHSiCl_2$, $SiCl_4$, $EtSiCl_3$, $n\text{-}PrSiCl_3$, $Allyl\text{-}SiCl_3$, silacyclobutane, $Me_2EtSiCl$, $MeEtSiCl_2$, $t\text{-}BuMe_2SiCl$, and $Me_3SiCH_2C\equiv CCH_3$. In sum, the mixture included 10 to 30 weight percent of polysilanes based on a total weight of the mixture and 10 to 30 weight percent of polycarbosilanes based on a total weight of the mixture, representing 5 to 50 percent yields, respectively.

Comparative Example 1A

Comparative Example 1A was formed using the same procedure described above except that the alkyl halide (MeCl) was replaced with PhCl, which is not an aliphatic hydrocarbyl halide of this disclosure, and the reactor temperature was 200° C. Comparative Example 1A did not form significant quantities of polysilanes or polycarbosilanes.

Comparative Example 1 B

Comparative Example 1B was formed using the same procedure described above except that the alkyl halide (MeCl) was replaced with PhCl, which is not an aliphatic hydrocarbyl halide of this disclosure, and the reactor temperature was 500° C. Comparative Example 1B did not form significant quantities of polysilanes or polycarbosilanes.

Comparative Example 2A

Comparative Example 2A was formed using the same procedure described above except that the alkyl halide (MeCl) was replaced with HCl, which is not an aliphatic hydrocarbyl halide, and the reactor temperature was 200° C. Comparative Example 2A produced a mixture that includes trace amounts of $SiH_4$, $HSiCl_3$, and $SiCl_4$, none of which are polysilanes or polycarbosilanes.

Comparative Example 2B

Comparative Example 2B was formed using the same procedure described above except that the alkyl halide (MeCl) was replaced with HCl, which is not an aliphatic hydrocarbyl halide, and the reactor temperature was 500° C. Comparative Example 2B still produced a mixture that included trace amounts of $SiH_4$, $HSiCl_3$, and $SiCl_4$, none of which are polysilanes or polycarbosilanes.

Comparative Example 3A

Comparative Example 3A was formed using the same procedure described above except that the alkyl halide (MeCl) was replaced with $PrSiCl_3$, which is not an aliphatic hydrocarbyl halide of this disclosure, and the reactor temperature was 200° C. Comparative Example 3A produced a mixture that included trace amounts of $PrSiH_3$, $PrSiHCl_2$, $SiCl_4$, and Allyl-$SiCl_3$, none of which are polysilanes or polycarbosilanes.

Comparative Example 3B

Comparative Example 3B was formed using the same procedure described above except that the alkyl halide (MeCl) was replaced with $PrSiCl_3$, which is not an aliphatic hydrocarbyl halide of this disclosure, and the reactor temperature was 500° C. Comparative Example 3B still produced a mixture that included trace amounts of $PrSiH_3$, $PrSiHCl_2$, $SiCl_4$, and Allyl-$SiCl_3$, none of which are polysilanes or polycarbosilanes.

The aforementioned results demonstrate that the instant disclosure produces results that are both superior to, and unexpected, over the comparative examples. More specifically, these results demonstrate that this disclosure produces polysilanes and polycarbosilanes in high yield using a method that is time and cost effective and that allows the mixture to be formed in a predictable and controlled manner. Moreover, the components used in this method can be easily recycled and/or re-used in other processes.

Examples 4-10

The reaction apparatus used in examples 4-9 comprised a 4.8 mm inner diameter quartz glass tube in a flow reactor. The reactor tube was heated using a Lindberg/Blue Minimite 2.54 cm tube furnace. $H_2$ was delivered via a Brooks Delta mass flow controller, and Ar was delivered via an Omega FMA 5500 mass flow controller. A stainless steel aliphatic hydrocarbyl halide bubbler was used to introduce the aliphatic hydrocarbyl halide into the $H_2$ gas stream. The amount of aliphatic hydrocarbyl halide in the $H_2$ gas stream was adjusted by changing the temperature of the aliphatic hydrocarbyl halide in the bubbler.

The reactor effluent, which contained the reaction product was passed through an actuated 6-way valve (Vici) with constant 100 μL injection loop before being discarded. Samples were taken from the reaction stream by actuating the injection valve and the 100 μL sample passed directly into the injection port of a 7890A Agilent GC-MS for analysis with a split ratio at the injection port of 100:1. The GC contained one Restek DCA column used and connected only to a mass spectrometer (Agilent 7895C MSD) for sensitive detection of trace products and positive identification of any products that formed. The column was heated by the GC oven.

In each of examples 4-10, an activated $Mg_2Si$ catalyst was prepared as follows: 0.5 g $Mg_2Si$ (Sigma Aldrich, 99+%) was charged into a quartz glass tube and placed into a flow reactor. Activation of substrate/catalyst was performed by flowing $H_2$ at 100 sccm (controlled via Brooks Delta mass flow controller) into the glass tube containing the catalyst in the reactor at 500° C. for 1-2 hours. The heating was accomplished using a Lindberg/Blue Minimite 2.54 cm tube furnace.

In example 4, activated $Mg_2Si$ catalyst (0.5 g), prepared as described above, was reacted with H2/CH2Cl2 at a flow rate of 3-5 sccm, 400° C., and atmospheric pressure. The reaction was periodically sampled and analyzed by GC/GC-MS as described above to determine the Si-containing species leaving the reactor. The mixture formed using the aforementioned procedure was comprised of numerous linear silmethylenes and silethylenes, including $Cl_2MeSi$—$CH_2$—$SiMeCl_2$, $Cl_3Si$—$CH_2$—$SiCl_3$, $MeCl_2Si$—$CH_2$—$SiCl_3$, and $Cl_3Si$—$(CH_2)_2$—$SiCl_3$. The mixture also contained linear siloxanes including $Cl_3Si$—O—$SiCl_3$. In addition, the mixture included various Si monomers including $Me_4Si$, $Me_3SiCl$, $Me_2SiCl_2$, $MeSiCl_3$, $SiCl_4$, and $EtSiCl_3$. Several hydrocarbons also comprised the mixture, including linear $C_xH_y$, where $0<x<5$ and $0<y<12$, 2,2-dimethylbutane, 2,2-dimethylpropane, 2,2-dimethylpentane, neo-pentane, iso-pentane, neo-hexane, iso-hexane, chloromethane and dichloroethane.

In example 5, activated $Mg_2Si$ catalyst (0.5 g), prepared as described above, was reacted with $Ar/CHCl_3$ at a flow rate of 3-5 sccm, 400° C., and atmospheric pressure. The reaction was periodically sampled and analyzed by GC/GC-MS as described above to determine the Si-containing species leaving the reactor. The mixture formed using the aforementioned procedure was comprised of linear silmethylenes, including $Cl_3Si$—$(CH_2)_2$—$SiCl_3$. The mixture also contained linear siloxanes including $Cl_3Si$—O—$SiCl_3$. In addition, the mixture included various Si monomers including $MeSiCl_3$, $SiCl_4$, and $HSiCl_3$. Several hydrocarbons also comprised the mixture, including linear $C_xH_y$, where $3<x<5$ and $8<y<12$, 2-methylpropane, iso-pentane, benzene, toluene, hydrogen chloride, vinylchloride, chloroethene, chloropropane, chloropropene, dichloroethane, dichloroethene, trichloroethylene, tetrachloroethylene, and perchloroethane.

In example 6, activated $Mg_2Si$ catalyst (0.5 g), prepared as described above, was reacted with $H_2/CHCl_3$ at a flow rate of 3-5 sccm, 400° C., and atmospheric pressure. The reaction was periodically sampled and analyzed by GC/GC-MS as described above to determine the Si-containing species leaving the reactor. The mixture formed using the aforementioned procedure was comprised of linear silmethylenes, including $Cl_3Si$—$(CH_2)_2$—$SiCl_3$. The mixture also contained linear siloxanes including $Cl_3Si$—O—$SiCl_3$. In addition, the mixture included various Si monomers including $MeSiCl_3$, $SiCl_4$, and $HSiCl_3$. Several hydrocarbons also comprised the mixture, including linear $C_xH_y$, where $2<x<3$ and $4<y<8$, 2-methylpropane, iso-butane, iso-pentane, iso-hexane, ethylchloride, vinylchloride, dichloroethene, and perchloroethane.

In example 7, activated $Mg_2Si$ catalyst (0.5 g), prepared as described above, was reacted with $H_2/CCl_4$ at a flow rate of 3-5 sccm, 400° C., and atmospheric pressure. The reaction was periodically sampled and analyzed by GC/GC-MS as described above to determine the Si-containing species leaving the reactor. The mixture formed using the aforementioned procedure was comprised of linear silmethylenes, including $Cl_3Si$—$(CH_2)_2$—$SiCl_3$. The mixture also contained linear siloxanes including $Cl_3Si$—O—$SiCl_3$. In addition, the mixture included various Si monomers including $SiCl_4$ and HSiCl$_3$. Several hydrocarbons also comprised the mixture, including linear C$_x$H$_y$, where 2<x<3 and 4<y<8, 2-methylpropane, iso-butane, iso-pentane, iso-hexane, hydrogen chloride, methylchloride, vinylchloride, dichloromethane, dichloroethene, chloroform, trichloroethylene, hexachlorobutadiene, pentachloroethane, perchloroethane and perchloroethylene.

In example 8, activated Mg$_2$Si catalyst (0.5 g), prepared as described above, was reacted with H$_2$/CCl$_4$ at a flow rate of 3-5 sccm, from 200° C.-450° C., and atmospheric pressure. The reaction was periodically sampled and analyzed by GC/GC-MS as described above to determine the Si-containing species leaving the reactor. The mixture formed using the aforementioned procedure included linear siloxanes including Cl$_3$Si—O—SiCl$_3$. In addition, the mixture included a Si monomer including SiCl$_4$. Several hydrocarbons were also present the mixture, including ethane, propene, dichloromethane, chloroform, hydrogen chloride, trichloroethylene, tetrachloroethylene, pentachloroethane, hexachlorobutadiene, dichloroethyne, perchloroethylene, and perchloroethane.

In examples 7 and 8, perchloroethylene and perchloroethane were the major components in the reactor effluent. Without wishing to be bound by theory, it is thought that at the lower temperatures (e.g. 200° C. to 400° C.), the Mg$_2$Si is acting as a catalyst, not as a reactant, i.e., silicon source.

In example 9, activated Mg$_2$Si catalyst (0.5 g), prepared as described above, was reacted with H$_2$/CCl$_4$ at a flow rate of 3-5 sccm, 475° C.-600° C., and atmospheric pressure. The reaction was periodically sampled and analyzed by GC/GC-MS as described above to determine the Si-containing species leaving the reactor. The mixture formed using the aforementioned procedure included primarily various Si monomers including SiCl$_4$ and HSiCl$_3$. In addition, the mixture further comprised lesser amounts of hydrocarbons and chlorinated hydrocarbons including methane, ethene, propene, dichloromethane, chloroform, hydrogen chloride, and perchloroethylene.

In example 10, Mg$_2$Si catalyst (0.5 g), prepared as described above, was reacted with H$_2$/CH$_3$Cl at a flow rate of 5 sccm, 400° C., and atmospheric pressure. The reaction was periodically sampled and analyzed by GC/GC-MS as described above to determine the Si-containing species leaving the reactor. The mixture formed using the aforementioned procedure was comprised of numerous linear, branched, and cyclic polycarbosilanes, including Me$_2$HSi—CH$_2$—SiHMe$_2$, Me3Si—CH$_2$—SiHMe$_2$, Me$_3$Si—CH$_2$—SiMe$_3$, cis-Me$_3$Si—(CH)$_2$—SiMe$_3$, Me3Si—(CH$_2$)$_2$—SiMe$_3$, trans-Me$_3$Si—(CH)$_2$—SiMe$_3$, Me$_3$Si—CH$_2$—(SiMe$_2$—CH$_2$)$_2$—SiMe$_3$, EtMe$_2$Si—CH$_2$, —SiMe$_2$Et, Me$_3$Si—(CHCH$_3$)—SiMe$_3$, ClMe$_2$Si—CH$_2$—SiMe$_3$, Me$_2$HSi—CH$_2$—SiMe$_3$, ClMe$_2$Si—CH$_2$—SiMe$_2$Cl, Me$_3$Si—CH$_2$—SiMe$_2$—SiMe$_3$, (Me$_3$Si—CH$_2$)$_2$—SiMeH, Me$_3$Si—CH$_2$—SiH(CH$_2$OH)—CH$_2$—SiMe$_3$, Me$_3$Si—CH$_2$—SiMe$_2$—CH$_2$—SiMe$_3$, (Me$_3$Si)$_3$—CH, 1,1,3,3-tetramethyl-1,3-disilacyclobutane, 1,1,3,3,5-Pentamethyl-1,3,5-trisilacyclohexane, and 1,1,3,3, 5,5-Hexamethyl-1,3,5-trisilacyclohexane. Additionally, linear and cyclic polylsilanes were observed, including Me$_2$HSi—SiHMe$_2$, Me$_3$Si—SiHMe$_2$, Me$_3$Si—SiMe$_3$, Me$_3$Si—Si(CH$_2$CH$_3$)Me$_2$, Me$_3$Si—SiMe$_2$—SiMe$_3$, 1,1,2,2-tetramethyl-1,2-disilacyclopentane, and 1,1,2,2-tetramethyl-1,2-disilacyclohexane. The mixture also contained linear siloxanes including Me$_3$Si—O—SiMe$_3$. In addition, the mixture included various Si monomers including Me$_2$SiH$_2$, Me$_3$SiH, Me$_4$Si, EtMe$_3$Si, Me$_3$Si(CHCHCH$_3$), Me$_3$Si(CH$_2$CHCH), Me$_3$SiC(CH$_3$)CH$_2$CH$_3$, (C$_6$H$_{11}$)Me$_2$SiOMe, Me$_3$SiOPh, Me$_3$SiCl, EtMe$_2$SiCl, Me$_2$SiCl2, MeSiCl$_3$, SiCl$_4$, EtSiCl$_3$, 1-methyl-4-methylene-2-(trimethylsilyl)cyclopentene, and Tetracyclo[4.2.1.0(3,8).0(4,7)]non-9-ene, 9-(trimethylsilyl)-. Several hydrocarbons also comprised the mixture, including linear C$_x$H$_y$, where 0<x<3 and 0<y<8, 2-methylpropene, 2,2-dimethylbutane, 2,2-dimethylpropane, 2,2-dimethylpentane, iso-butane, neo-pentane, iso-pentane, neo-hexane, iso-hexane, dimethylcyclopropane, 2-methyl-2-butene, 3-methyl-2-pentene, 2,3-dihydro-3-methylfuran, 3-hexen-2-one, cyclohexane, o-xylene, p-xylene, m-xylene, ethyltoluene, and trimethylbenzene.

It is to be understood that one or more of the values described above may vary by ±5%, ±10%, ±15%, ±20%, ±25%, or ±30%. so long as the variance remains within the scope of the disclosure. It is also to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The subject matter of all combinations of independent and dependent claims, both singly and multiply dependent, is herein expressly contemplated but is not described in detail for the sake of brevity. The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

What is claimed is:

1. A method of forming a reaction product, said method comprising a step of combining a metal silicide and an aliphatic hydrocarbyl halide in a reactor at a temperature of from 200° C. to 600° C. to form the reaction product wherein the metal silicide comprises a Group I or Group II metal, wherein the reaction product comprises at least one polysilane and/or at least one polycarbosilane, and wherein the polysilane has formula $R_3Si(R_2Si)_mSiR_3$ wherein each R is independently $C_1$-$C_4$ alkyl, halo, or —H, and m has an average value of from 1 to 5; and the polycarbosilane has formula $R^2{}_3Si$—$CH_2$($R^2{}_2Si$—$CH_2)_nSiR^2{}_3$ wherein each $R^2$ is independently $C_1$-$C_4$ alkyl, halo, or —H, and n has an average value of from 1 to 5.

2. A method as set forth in claim 1 wherein the metal silicide is further defined as $Mg_2Si$.

3. A method as set forth in claim 1 wherein the aliphatic hydrocarbyl halide is further defined as an alkyl halide of formula RX, wherein R is $C_1$-$C_{10}$ alkyl and wherein X is halo.

4. A method as set forth in claim 3 wherein X is chloro.

5. A method as set forth in or claim 4 wherein R is further defined as methyl.

6. A method as set forth in claim 1 wherein the reaction product comprises at least two polysilanes and at least one of the polysilanes is branched.

7. A method as set forth in claim 1 wherein the reaction product comprises at least two polysilanes and at least one of the polysilanes is cyclic.

8. A method as set forth in claim 1 wherein the reaction product further comprises at least one hybrid polysilane-carbopolysilane having the formula $R_3{}^3Si$—$[SiR^3{}_2]_m$[$SiR^3{}_2CH_2]_nSiR^3{}_3$ wherein each $R^3$ is independently $C_i$-$C_4$ alkyl, halo, or —H, m has a value of 1 to 5 and n has an average value of from 1 to 5.

9. A method as set forth in claim 1 wherein the reaction product comprises at least two polycarbosilanes and at least one of the polycarbosilanes is branched.

10. A method as set forth in claim 1 wherein the reaction product comprises at least two polycarbosilanes and at least one of the polycarbosilanes is cyclic.

11. A method as set forth in claim 10 wherein the cyclic polycarbosilane is selected from the group of 1,1,3,3-tetramethyl-1,3 disilacyclobutane, 1,1,3,3,-tetramethyl-1,3-disilacyclopentane, 1,1,3,3,5-pentamethyl-1,3,5-trisilacylohexane, 1,1,3,3,5,5-hexamethyl-1,3,5-trisilacylohexane, and combinations thereof.

12. A method as set forth in claim 1 wherein the reaction product comprises at least one silicon monomer selected from the group of $Me_4Si$, $Me_3SiH$, $Me_3SiCl$, $Me_2SiCl_2$, $Me_2HSiCl$, $MeSiCl_3$, $MeHSiCl_2$, $SiCl_4$, $EtSiCl_3$, n-$PrSiCl_3$, Allyl-$SiCl_3$, silacyclobutane, $Me_2EtSiCl$, $MeEtSiCl_2$, t-$BuMe_2SiCl$, $Me_3SiCH_2C$≡$CCH_3$, and combinations thereof.

13. A method as set forth in claim 1 wherein the method is further defined as continuous and the reactor is further defined as a fluidized bed reactor.

14. A method as set forth in claim 1 wherein the reactor temperature is further defined as from 325° C. to 500° C.

15. A method as set forth in claim 1 wherein the metal silicide and the aliphatic hydrocarbyl halide react in the reactor at a pressure that exceeds atmospheric pressure.

16. A method as set forth in claim 1, wherein the aliphatic hydrocarbyl halide is a compound of formula $H_aC_bX_c$, where subscript a is an integer of 0 or more, subscript b is an integer of 1 or more, and subscript c is an integer of 1 or more.

17. A method as set forth in claim 16, where subscript c is an integer of 2 or more.

* * * * *